US 6,537,546 B2

(12) United States Patent
Echigo et al.

(10) Patent No.: US 6,537,546 B2
(45) Date of Patent: Mar. 25, 2003

(54) PROCESS FOR MACROMOLECULARIZING PHENOLIC COMPOUNDS ETC. AND USE THEREOF

(75) Inventors: Takashi Echigo, Chiba (JP); Ritsuko Ohno, Tokyo (JP)

(73) Assignee: SDS Biotech K.K., Tokyo (JP)

( * ) Notice: Subject to any disclaimer, the term of this patent is extended or adjusted under 35 U.S.C. 154(b) by 0 days.

(21) Appl. No.: 09/742,217

(22) Filed: Dec. 22, 2000

(65) Prior Publication Data

US 2001/0007762 A1 Jul. 12, 2001

Related U.S. Application Data

(62) Division of application No. 09/202,041, filed as application No. PCT/JP97/01694 on May 20, 1997, now Pat. No. 6,190,891.

(30) Foreign Application Priority Data

Jun. 6, 1996 (JP) .............................................. 8/144200

(51) Int. Cl.[7] ........................... A61K 38/44; C12P 13/00
(52) U.S. Cl. ................... 424/94.4; 435/128; 435/254.1; 435/911; 435/189
(58) Field of Search .............................. 435/128, 254.1, 435/911, 189; 424/94.4

(56) References Cited

U.S. PATENT DOCUMENTS

| 2,485,587 A | * | 10/1949 | Goss .......................... 106/163 |
|---|---|---|---|
| 4,432,921 A | * | 2/1984 | Haars ......................... 264/109 |
| 4,752,509 A | | 6/1988 | Simonson et al. |
| 4,770,997 A | * | 9/1988 | Yoshino ....................... 435/25 |
| 5,795,885 A | * | 8/1998 | Schneider .................... 510/376 |
| 5,846,788 A | | 12/1998 | Pederson et al. |

FOREIGN PATENT DOCUMENTS

| JP | 6-316874 | 11/1994 |
|---|---|---|
| JP | 8-332032 | 12/1996 |

OTHER PUBLICATIONS

"Novo employs enzymes to bond wood fibers", *European Chemical News*, p. 38, 15–21. Apr. 1996.

* cited by examiner

*Primary Examiner*—Irene Marx
(74) *Attorney, Agent, or Firm*—Sughrue Mion, PLLC

(57) ABSTRACT

A process for macromolecularizing phenolic compounds or aromatic amine compounds by the action of a catalyst comprising an enzyme having a polyphenol oxidizing activity in the alkali region; applications of the compounds obtained by the above process to thickeners, stabilizers, coagulants, emulsifiers, dispersants, water retainers, antioxidants, adhesives, concrete admixtures, dyes, coating materials, petroleum recovering agent, soil conditioner, a blow-applied seed bearing surface soil stabilizer, deodorants, smell eliminators, agricultural chemical spreaders, feeding stuff binders, bactericides, antimicrobial agents, viral infection inhibitors, bioadhesion preventives, biotic repellents, insecticides, poultices, ink bases or wood treating agents; and method of waste water disposal, a method of deoxygenation and a method of treating wood, concrete or soil in which use is made of the above reaction.

13 Claims, No Drawings

PROCESS FOR MACROMOLECULARIZING PHENOLIC COMPOUNDS ETC. AND USE THEREOF

This is a divisional application of application Ser. No. 09/202,041, filed Dec. 7, 1998, and issued on Feb. 20, 2001, as U.S. Pat. No. 6,190,891, the disclosure of which is incorporated herein by reference, which is a 371 of PCT/JP 97/01694 filed May 20, 1997.

TECHNICAL FIELD

The present invention relates to a process for enzymatic macromolecularization of phenolic compounds or aromatic amine compounds and to applications of the macromolecules obtained by the process.

More particularly, the present invention provides a process for producing phenolic compounds or aromatic amine compounds which have increased molecular weights by reacting phenolic compounds or aromatic amine compounds with an enzyme having a polyphenol oxidizing activity in the alkaline pH region, and applications of the reaction method of increasing the molecular weight of phenolic compounds or aromatic amine compounds utilizing the above-described catalytic activity of the enzyme in the alkali regions to obtain thickeners, stabilizers, coagulants, emulsifiers, dispersants, water retainers, antioxidants, adhesives, concrete admixtures, dyes, deodorants, smell eliminators, coating materials, petroleum recovering agents, soil conditioners, blow-applied seed bearing surface soil stabilizers, agricultural chemical spreaders, feeding stuff binders, bactericides, antimicrobial agents, viral infection inhibitors, bioadhesion preventives, biotic repellents, insecticides, poultices, ink bases and wood treating agents; a method of producing these various agents; a method of waste water disposal; a method of deoxygenation; and methods of treating wood, concrete and soil, respectively.

BACKGROUND ART

Hitherto, it has been known that phenolic compounds etc. can be macromolecularized by utilizing an enzyme such as laccase or polyphenol oxidase produced by Basidiomycotina or Deuteromycotina (Journal of Biotechnology, 13, 229–241, 1990 and etc. so on). However, the laccases or polyphenol oxidases produced by fungi have their optimal reaction pH in the acidic region so that the reaction must be carried out in pH region ranging from acidic to neutral in order to catalyze or accelerate the macromolecularization reaction utilizing these enzymes and in addition, the rate of the macromolecularization reaction is not high enough. Also, the natural organic compounds with which these enzymes react are mainly polyphenolic compounds and, hence, the reaction must be carried out in the pH region ranging from acidic to neutral because the optimal reaction pH of the enzyme is in the acidic region despite the fact that the polyphenolic compounds have solubilities which decrease in the pH region from acidic to neutral, resulting in a defect that it is impossible to efficiently macromolecularize polyphenolic compounds in high concentrations. Further, although many polyphenolic compounds are accelerated their autooxidation in the alkaline pH region, enzymatic oxidative macromolecularization has been carried out in the pH region ranging from acidic to neutral, resulting in a defect that the autooxidation cannot be utilized effectively.

Further, it has been known that phenolic compounds, etc. can be macromolecularized with bilirubin oxidase, too, and this reaction can be utilized in the macromolecularization of lignin and dying of cotton (WO95-01426, and JP-A-6-316874). However, in the prior art using bilirubin oxidase, the enzyme-catalytic macromolecularization of phenolic compounds, etc., is carried out in the pH region ranging from acidic to neutral and therefore the macromolecularization reaction rate is not sufficiently high or there is no description suggesting that the macromolecularization reaction of phenolic compounds is accelerated in the alkaline pH region by bilirubin oxidase.

OBJECT OF THE INVENTION

An object of the present invention is to provide a process of enzyme-catalytically macromolecularizing phenolic compounds or aromatic amine compounds in the alkaline pH region.

Another object of the present invention is to provide a process of producing thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives, biotic repellents, insecticides, poultices, ink bases and wood treating agents, comprising the step of efficiently macromolecularizing phenolic compounds or aromatic amine compounds using an enzyme having a polyphenol oxidizing activity in the alkaline pH region.

Still another object of the present invention is to provide thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives, biotic repellents, insecticides, poultices, ink bases and wood treating agents, comprising the macromolecules obtained by efficiently macromolecularizing the above-described phenolic compounds or aromatic amine compounds.

Yet another object of the present invention is to provide a method of treating waste water containing phenolic compounds or aromatic amine compounds, in which the above-described compounds are disposed from the waste water by utilizing the above-described macromolecularization reaction according to the present invention.

Further, yet another object of the present invention is to provide a method of deoxygenation in which the above-described macromolecularization reaction according to the present invention is utilized to remove dissolved oxygen.

Further, object of the present invention is to provide a method of treating wood utilizing the above-described macromolecularization reaction according to the present invention.

Further, an object of the present invention is to provide a method of treating concrete utilizing the above-described macromolecularization reaction according to the present invention.

Furthermore, an object of the present invention is to provide a method of improving the soil utilizing the above-described macromolecularization reaction according to the present invention.

DISCLOSURE OF THE INVENTION

The present inventors have made intensive investigation in order to develop a process of efficiently macromolecularizing phenolic compounds or aromatic amine compounds. As a result, they have now found that, surprisingly, use of a suitable enzyme having a polyphenol oxidizing activity in the alkaline region, particularly in the alkaline pH region not lower than pH 8, results in the achievement of efficient macromolecularization of phenolic compounds or aromatic amine compounds, thus completing the present invention.

Accordingly, the present invention provides the followings:

1) A process of producing phenolic compounds or aromatic amine compounds having increased molecular weights, characterized by comprising allowing an enzyme having a polyphenol oxidizing activity to act on phenolic compounds or aromatic amine compounds in the alkaline pH region to macromolecularize them.
2) The process as described in 1) above, characterized in that the macromolecularization is carried out in the alkaline pH region of not lower than pH 8.
3) The process as described in 1) or 2) above, characterized in that as the enzyme having a polyphenol oxidizing activity is used one or more of catechol oxidase, laccase, polyphenol oxidase, ascorbic acid oxidase or bilirubin oxidase.
4) The process as described in any one of 1) to 3), wherein use is made of an enzyme having a polyphenol oxidizing activity obtained by cultivating a bacterium belonging to the genus Bacillus.
5) The process as described in 4) above, wherein the enzyme having a polyphenol oxidizing activity is an enzyme obtained by cultivating *Bacillus licheniformis* or *Bacillus natto*.
6) The process as described in 5) above, wherein the enzyme having a polyphenol oxidizing activity is an enzyme obtained by cultivating *Bacillus licheniformis* SD3003 (Accession No. FERM BP-5801).
7) The process as described in any one of 1) to 3) above, wherein the enzyme having a polyphenol oxidizing activity is an enzyme obtained by cultivating a fungus belonging to the genus Myrothecium.
8) The process as described in 7) above, wherein the enzyme having a polyphenol oxidizing activity is an enzyme obtained by cultivating *Myrothecium verrucaria* or *Myrothecium roridum*.
9) The process as described in 8) above, wherein the enzyme having a polyphenol oxidizing activity is an enzyme obtained by cultivating *Myrothecium verrucaria* SD3001 (Accession No. FERM BP-5520) or *Myrothecium roridum* SD3002 (Accession No. FERM BP-5523).
10) The process as described in any one of 1) to 9) above, wherein the enzyme having a polyphenol oxidizing activity is an enzyme which has an optimal reaction pH in the alkaline region of not lower than pH 7.5 when the activity thereof is measured with syringaldazine.
11) The process as described in any one of 1) to 10) above, wherein the phenolic compound is lignin or a lignin derivative.
12) The process as described in 11) above, wherein the lignin derivative is lignosulfonic acid.
13) The process as described in any one of 1 to 10) above, wherein the phenolic compound is flavonoid.
14) The process as described in any one of 1) to 13) above, characterized in that the macromolecularization reaction is carried out by adding one or more of a quinone compound, unsaturated fatty acid, unsaturated alcohol or an unsaturated alkyl compound to the phenolic compound or aromatic amine compound.
15) The process as described in any one of 1) to 14) above, wherein an antimicrobial compound, an antiviral compound, a biotic repellent compound, an insecticidal compound or a metal ion coexists.
16) The process as described in any one of 1) to 15) above, wherein the macromolecularization is carried out at a temperature of 0 to 100° C.
17) Thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives, biotic repellents, insecticides, poultices, ink bases or wood treating agents, comprising macromolecular compound produced by the process as described in any one of 1) to 16) above.
18) A process of producing thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives, biotic repellents, insecticides, poultices, ink bases or wood treating agents, comprising the step of macromolecularizing the phenolic compounds or aromatic amine compounds as described in any one of 1) to 16) above.
19) A method of disposing of waste water, characterized by comprising macromolecularizing phenolic compounds or aromatic amine compounds in waste water in accordance with the method as described in any one of 1) to 16) above and removing it from the waste water.
20) A deoxygenating agent for use in the alkaline pH region, characterized by comprising a phenolic compound or aromatic amine compound and the enzyme having a polyphenol oxidizing activity as described in any one of 1) to 16) above.
21) A method of treating wood, characterized by comprising impregnating wood with an enzyme having a polyphenol oxidizing activity together with a phenolic compound or aromatic amine compound and macromolecularizing the phenolic compound or aromatic amine compound in the wood.
22) A method of treating concrete, characterized by comprising adding to concrete an enzyme having a polyphenol oxidizing activity together with a phenolic compound or aromatic amine compound and macromolecularizing the phenolic compound or aromatic amine compound in the concrete.
23) A method of treating soil, characterized by comprising adding to soil an enzyme having a polyphenol oxidizing activity together with a phenolic compound or aromatic amine compound and macromolecularizing the phenolic compound or aromatic amine compound in the soil.

DETAILED DESCRIPTION OF THE INVENTION

[Polyphenol Oxidase]

The enzymes used for the purposes of the present invention may be any enzyme that has a polyphenol oxidizing activity at alkaline pH values. Examples of such an enzyme include polyphenol oxidases such as catechol oxidase, laccase, polyphenol oxidase, ascorbic acid oxidase, bilirubin oxidase, or the like produced by microorganisms, for example fungi or bacteria, or plants. Besides these enzymes, any enzyme protein that has a polyphenol oxidizing activity at alkaline pH values may also be used in the present invention.

As the enzyme to be used in the present invention, having a polyphenol oxidizing activity in the alkaline pH region, those enzymes are desirable which have optimal reaction pH for polyphenol oxidation reaction in the alkaline region of not lower than pH 7.5 in order to carry out efficient macromolecularization reaction. More specifically, it is desirable that such enzymes have optimal reaction pH in the alkaline region of not lower than pH 7.5 when the activity thereof is measured with syringaldazine that is described later.

Examples of the microorganisms which produce the enzymes used for the purposes of the present invention include the followings.

As fungi, there can be cited those strains which belong to the genera falling in Deuteromycotina, i.e., Aspergillus, Botrytis, Myrothecium, Penicillium, Pestalotia, Rhizoctonia, Tricoderma, preferably *Aspergillus nidulans, Botrytis cinerea, Myrothecium roridum, Myrothecium verrucaria, Myrothecium prestonii, Myrothecium leucotrichum, Penicillium sclerotiorum, Penicillium janthinellum, Pestalotia palmarum, Rhizoctonia praticola, Tricoderma resii,* and *Tricoderma viride.* Of these, particularly preferred are *Myrothecium verrucaria* SD3001 (Deposited under Accession No. FERM P-14955 at Research Institute of Biotechnological & Industrial Science, Institute of Industrial Science and Technology, Ministry of International Trade and Industry, at 1–3, Higashi 1-chome, Tsukuba-shi, Ibaragi-ken, Japan on May 29, 1995 and transferred to international deposition under Accession No. FERM BP-5520 on Apr. 24, 1996) or *Myrothecium roridum* SD3002 (Deposited under Accession No. FERM P-15255 at Research Institute of Biotechnological & Industrial Science, Institute of Industrial Science and Technology, Ministry of International Trade and Industry, at 1–3, Higashi 1-chome, Tsukuba-shi, Ibaragi-ken, Japan on Oct. 29, 1995 and transferred to international deposition under Accession No. FERM BP-5523 on Apr. 24, 1996).

Other preferred fungi include those strains which belong to the genera falling in Basidiomycotina, i.e., Pleurotus, Lentinus, Schizophyllum, Armillariella, Flammulina, Agaricus, Coprinus, Phanerochaete, Phlebia, Lenzites, Melanoleuca, Pholiota, Stereumu, Polyporus, Polyporellus, Microporus, Fomitopsis, Pycnoporus, Trametes, Coriolus, Daedaleopsis, Rigidoporus, Fomes, Ganoderma, Trachyderma, Hymenochaete, and Inonotus, preferably *Pleurotus cornucopiae, Pleurotus osteratus, Lentinus edodes, Schizophyllum commune, Armillariella mellea, Flammulina velutipes, Agaricus bisporus, Coprinus comatus, Coprinus cinereus, Coprinus congregatus, Phanerochaete chrysosporium, Phlebia radiata, Lenzites betulina, Melanoleuca verrucipes, Pholiota nameko, Stereumu hirsutum, Polyporus squamosus, Polyporellus badius, Microporus flabelliformis, Fomitopsis pinicola, Pycnoporus coccineus, Trametes orientalis, Coriolus versicolor, Coriolus hirsutus, Daedaleopsis tricolor, Rigidoporus zonalis, Fomes fomentarius, Ganoderma lucidum, Trachyderma tsunodae, Hymenochaete rubiginosa,* and *Inonotus mikadoi.*

Other preferred fungi include those strains which belong to the genera falling in Ascomycotina, i.e., Podospora, Neurospora, and Monocillium, preferably *Podospora anserina, Neurospora crassa,* and *Monocillium indicum.*

Preferred bacteria include those strains belonging to *Bacillus alcalophilus, Bacillus amyloliquefaciens, Bacillus brevis, Bacillus firmus, Bacillus licheniformis, Bacillus natto, Bacillus pumilus, Bacillus sphaericus,* and *Bacillus subtilis,* preferably *Bacillus licheniformis,* and *Bacillus natto.* Of these, particularly preferred is *Bacillus lichenifor-*

*mis* SD3003 (Deposited under Accession No. FERM P-15383 at Research Institute of Biotechnological & Industrial Science, Institute of Industrial Science and Technology, Ministry of International Trade and Industry, at 1–3, Higashi 1-chome, Tsukuba-shi, Ibaragi-ken, Japan on Dec. 28, 1995 and transferred to international deposition under Accession No. FERM BP-5801 on Jan. 28, 1997).

Other preferred bacteria include those strains which belong to the genera Azospirillum, preferably *Azospirillum lipoferum* or those strains which belong to the genera falling in Actinomycetales, for example, Streptomyces, preferably *Streptomyces antibioticus,* or Aerobacter, preferably *Aerobacter aerogenes.*

Some preferred plants which contains enzymes used in the present invention include *Acer pseudoplatanum,* Dioscorea, Abelmoschus, Psidium, Helianthus, potato, apple, pumpkin, cucumber, wheat, alfalfa, etc.

[Preparation of Enzymes]

The enzymes used in the present invention can be obtained by cultivating strains belonging to the above-described microorganisms, for example fungi or bacteria, and variants thereof. Besides, they can also be prepared by utilizing genetically engineered microorganisms. That is, the enzymes can be produced by cultivating, under conditions enabling expression of enzyme proteins, host cells transformed with an expression vector which includes a DNA vector having a replication initiator codon for replicating a vector in the host organism, the vector having inserted therein a DNA sequence encoding the above-described enzyme protein together with suitable promoter, operator, and terminator DNA sequences having an enzyme expressing function in the host organism, or host cells transformed by incorporating in the host cell DNA, a DNA sequence encoding the above-described enzyme together with suitable promoter, operator, and terminator DNA sequences which have an enzyme expressing function in the host organism, followed by recovering the enzyme protein from the culture medium.

The DNA fragments encoding the enzyme protein according to the present invention can be obtained by conventional methods such as the method in which cDNA or genome library from a strain belonging to the above-described microorganisms, for example fungi or bacteria, is used as an isolation source, and a target DNA fragment is identified using as a probe which is an oligonucleotide synthesized based on the amino acid sequence of the enzyme protein according to the present invention, the method in which a clone expressing the activity of an oxidase is screened, or the method in which a clone is screened which produces a protein that reacts with an antibody against the above-described enzyme protein.

It is possible to prepare the enzyme protein according to the present invention by extraction from seeds, fruits, leaves or the like of the above-described plants.

Further, in the cultivation of the strains belonging to fungi or bacteria and variants thereof for obtaining the enzyme protein according to the present invention, there can be used synthetic medium and nutrition medium containing organic carbon sources and organic nitrogen sources which are employed conventionally. In the case of cultivation, it is desirable that $Cu^{2+}$ ions be added in amounts of 0.001 mM to 10 mM, preferably 0.01 mM to 1 mM, as metal salt.

When it is secreted outside the cells of fungi or bacteria, the polyphenol oxidase according to the present invention can be recovered from the culture medium by a well-known method. The recovery procedure includes a series of operations such as removal of cells from the culture medium by centrifugation, filtration or membrane separation, and chromatography, for example ion exchange chromatography. Also, membrane concentration with ultrafiltration membrane is effectively employed. When it is accumulated inside the cells of fungi or bacteria or when it exists inside plant tissues, the enzyme protein can be recovered from the microbial cells or plant tissues by a well-known method. The recovery procedure includes a series of operations such as mechanical rupture of the tissue by homogenization, isolation and extraction of an enzyme protein solution by centrifugation, filtration or membrane separation, and chromatography, for example ion exchange chromatography. Also, membrane concentration with ultrafiltration membrane is effectively employed.

[Measurement Method of Activity]

In the present invention, the measurement of polyphenol oxidizing activity of the enzyme protein having a polyphenol oxidizing activity was carried out by conducting the reaction in an aqueous solution containing 20 ppm of syringaldazine and 100 mM Tris-HCl buffer or potassium phosphate buffer at an optimal reaction pH at 20° C. and measuring the absorbance at 525 nm. The amount of activity in which 1 $\mu$mol/minute of syringaldazine is oxidized was defined as 1 unit (hereafter, abbreviated as "U").

[Macromolecularization Method and Its Use]

In the process of producing phenolic compounds or aromatic amine compounds having increased molecular weights according to the present invention, the concentration of phenolic compounds or aromatic amine compounds is 0.01 to 90%, preferably 1 to 80%. The reaction temperature is 0 to 150° C., preferably 0 to 100° C. Further, the reaction pH is 7.0 to 12, preferably 7.5 to 10. The activity concentration of the enzyme to be used is 1 to 10,000 U/liter, preferably 10 to 2,000 U/liter. It is desirable that the enzyme activity concentration be adjusted depending on the purpose. That is, when more speedy macromolecularization and gelation or solidification is contemplated to be achieved, the reaction will be carried out at higher activity concentrations. On the other hand, when the reaction is carried out at lower activity concentrations, milder macromolecularization reaction will proceed, giving rise to a more homogeneous macromolecule solution as a liquid substance, and when the reaction is continued further, mild gelation reaction will proceed throughout the reaction mixture. When a suitable degree of macromolecularization is reached, the reaction can be terminated by the addition of alkali or alkali salts, such as NaOH, $NH_3$, $Na_2CO_3$, and $CaCO_3$, addition of acids such as hydrochloric acid, sulfuric acid, and nitric acid, addition of known enzyme inhibitors, or heat treatment such as that at 100° C. for 15 minutes.

The gelled phenolic compounds or aromatic amine compounds can optionally be molten again by heating at 50 to 230° C. Such a heat melting property is a useful property when the compounds are used in applications such as a dispersant, an adhesive and a coating composition. Also, it is possible to obtain phenolic compounds or aromatic amine compounds having very high molecular weights as a solution by addition of hot water or the like after the heat melting to disperse or dissolve the compounds above.

In order to accelerate the thermal curing, it is also possible to add polyols and the like such as furfuryl alcohol, sugars and etc. In order to have a physiologically active substance contained in the macromolecular compound to obtain an immobilized physiologically active substance or substance with a controlled release of physiologically active substance, it is also possible to carry out the macromolecularization with an antimicrobial compound, antiviral compound, a biotic repellent compound, an insecticidal compound or a metal ion coexisting, or to add an antimicrobial compound, antiviral compound, a biotic repellent compound, an insecticidal compound or a metal ion after the macromolecularization. As the antimicrobial compound, antiviral compound, biotic repellent compound, insecticidal compound or metal ion used for this purpose, there may be used many substances that have been known heretofore.

The macromolecularization reaction according to the present invention uses as an oxidation catalyst an enzyme having a polyphenol oxidizing activity and the oxygen in the air as an oxidizer, which makes it possible to apply the present invention to a wide field of applications. Further, when production of a large amount of macromolecule is contemplated, operations such as mechanical stirring of the reaction mixture and addition of air or oxygen to the reaction system are effective. Also, it is possible to carry out the reaction of the present invention in which oxygen is used as an oxidizer and the reaction in which hydrogen peroxide is used as an oxidizer simultaneously by adding to the reaction mixture peroxidase and hydrogen peroxide, or instead of hydrogen peroxide, an oxidase which can generate hydrogen peroxide and a substrate thereto.

[Phenolic Compounds or Aromatic Amine Compounds]

As the phenolic compounds or aromatic amine compounds to be macromolecularized in the present invention, there may be used any compound as far as the enzyme used in the present invention can oxidize it.

Specific examples of such phenolic compounds or aromatic amine compounds include lignin, lignosulfonic acid, humic acid, nitrohumic acid, tannin, catechin, gallic acid, urushiol, hesperidin, chlorogenic acid, hinokitiol, pyrocatechol, hydroquinone, t-butylhydroquinone, phenylhydroquinone, trimethylhydroquinone, ethyl 3,4-dihydroxycinnamic acid, pyrogallol, lauryl gallate, octyl gallate, syringic acid, ferulic acid, vanillin, o-vanillin, vanillic acid, vanillyl alcohol, ascorbic acid, 1,2-dihydroxynaphthalene, 2,3-dihydroxynaphthalene, 6,7-dihydroxy-2-naphthalenesulfonic acid, anthrarobin, alizarin, quinizarin, o-phenylenediamine, p-phenylenediamine, 3,4-diaminobenzophenone, o-anisidine, p-anisidine, o-aminophenol, p-aminophenol, 1,2-diaminoanthraquinone, and 1,4-diaminoanthraquinone.

Compounds other than these may also be used as a raw material for macromolecules or as a catalyst for the macromolecularization reaction as far as such compounds are substances that the enzyme used in the present invention can oxidize. Examples of such compounds include ABTS (2,2'-azobis(3-ethylbenzothiazoline-6-sulfonic acid)), bilirubin, isoascorbic acid, quercetin, rutin, guaiacol, 4-methoxyphenol, biphenol, 4,4'-ethylene-dianiline, methylhydroquinone, 1-hydroxybenzotriazole, 6-hydroxy-2,4,5-triaminopyrimidine, 4,5,6-triaminopyrimidine, 2,3-dihydroxypyridazine, 3,6-dihydroxypyridazine, 2,3-dihydroxypyridine, 4-hydroxy-3-methoxybenzoic acid, methyl 4-hydroxy-3-methoxybenzoate, 4,5-diamino-6-hydroxy-2-mercaptopyrimidine, 2,3-diaminopyridine, 2,5-dihydroxy-1,4-benzoquinone, 2,5-dihydroxybenzoic acid, 3,4-dihydroxybenzoic acid, 3,4-dihydroxy-3-cyclobuten-1,2-dione, 3-(3,4-dihydroxyphenyl)-L-alanine, 2-amino-3-hydroxypyridine, 3-amino-2-methoxydibenzofurane, 2,4-dimethoxyaniline, 2,5-dimethoxyaniline, 3,4-dimethoxyaniline, 2',5'-dimethoxyacetophenone, 3',4'-dimethoxyacetophenone, 1,4-dimethoxybenzene, veratrol, 2,3-dimethoxybenzoic acid, 2,5-diemethoxybenzoic acid, veratric acid, 3,4-dimethoxybenzyl alcohol, 3,4-dimethoxyphenethylamine, (3,4-dimethoxy-phenyl)acetic acid, (3,4-dimethoxyphenyl)acetonitrile, 4-allyl-2-methoxyphenol, 2-methoxy-4-propenylphenol, 2-methoxy-5-methylaniline, 2-methoxy-5-nitroaniline, 4-methoxy-2-nitroaniline, 3-methoxysalicylic acid, 3-methylcatechol, 4-methylcatechol, methylgallate, propylgallate, 3,4,5-trimethoxyaniline, 3,4,5-trimethoxyphenol, tropolone, purpurogallin, salicylaldoxime, 3-amino-5,6,7,8-tetrahydro-2-naphthol, 1,5-dihydroxynaphthalene, 3,5-dihydroxy-2-naphthoic acid, 4-hydroxy-1-naphthalenesulfonic acid, purpurin, 2,3-dihydro-9,10-dihydroxy-1,4-anthracenedione, and various azo dyes.

Also, in order to control the physical properties of the macromolecules, it is possible to use a plurality of such phenolic compounds or aromatic amine compounds in combination.

Upon producing macromolecularized phenolic compounds or aromatic amine compounds according to the present invention, quinone compounds may coexist which can be macromolecularized in a similar reaction path. Examples of such quinone compounds include anthraquinone-2-sulfonic acid, anthraquinone-1,5-disulfonic acid, anthraquinone-2,6-disulfonic acid, anthraquinone-2-carboxylic acid, 1-aminoanthraquinone, 2-aminoanthraquinone, anthrarufine, aminonaphthoquinone, 1,8-dihydroxyanthraquinone, camphorquinone, dehydroascorbic acid, 2-hydroxy-1,4-naphthoquinone, isatin, 5-nitroisatin, and various anthraquinone dyes. Also, it is possible to carry out air oxidation and macromolecularization simultaneously with enzymatic reaction under the coexistence of autooxidated substances, e.g., unsaturated fatty acids such as oleic acid and rinolic acid or unsaturated alcohols such as oleyl alcohol, or unsaturated alkyls such as squalene.

Of the macromolecularized phenolic compounds or aromatic amine compounds produced according to the present invention, particularly macromolecules of natural substances or derivatives thereof, such as lignin, lignosulfonic acid, humic acid, nitrohumic acid, tannin, catechin, gallic acid, urushiol, hesperidin, and hinokitiol, are highly useful because they are highly safe to environment as well as to humans so that making the best of their characteristics as high-molecular-weight compounds, they can be utilized in various fields of application such as thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives. biotic repellents, insecticides, poultices, ink bases and wood treating agents. It should be noted that in these applications, various additive components usually used in each field can be employed in combination.

Further, in these fields of application, it is possible to develop applications of higher functions of the high-molecular-weight compounds by macromolecularizing natural or non-natural phenolic compounds or aromatic amine compounds under milder reaction conditions in the production process of the present invention to control the physical properties such as viscosity, adhesion, water retention, water solubility, water resistance, resilience, and strength or physiological effects.

Also, in accordance with the present invention, a method of disposing waste water is possible in which the enzyme having a polyphenol oxidizing activity is allowed to act on waste water containing phenolic compounds or aromatic amine compounds in the alkaline pH region so that the phenolic compounds or aromatic amine compounds in the waste water can be macromolecularized and readily concentrated and the macromolecularized phenolic compounds or aromatic amine compounds can be separated and removed from the waste water. As the field of application and reaction substrate for which such an application is particularly useful, there can be cited lignin or lignin derivatives in the field of paper pulp and dyes such as azo dyes or anthraquinone dyes in the field of coloring and dying. By carrying out coagulation precipitation treatment by addition of a coagulant, activated carbon treatment, or filtration treatment after the macromolecularization reaction, the phenolic compounds or aromatic amine compounds in waste water can efficiently be concentrated so as to be separated and removed from the waste water.

Also, in accordance with the present invention, a deoxygenation method or production of a deoxygenating agent is also possible by allowing the enzyme having a polyphenol oxidizing activity to act on phenolic compounds or aromatic amine compounds in the alkaline pH region to have dissolved oxygen consumed. Such deoxygenation method and deoxygenating agent are very useful since many natural or non-natural phenolic compounds or aromatic amine compounds can be utilized therein and the concentration of dissolved oxygen can be decreased quickly.

Also, in accordance with the present invention, impregnation of the enzyme having a polyphenol oxidizing activity together with phenolic compounds or aromatic amine compounds into wood and macromolecularization, in the wood, of the phenolic compounds or aromatic amine compounds and in addition the polyphenol compounds such as lignin already contained in the wood enables improvement in workability in a drying step after the wood impregnation treatment, improvement in the strength of wood which was decreased due to lignin decomposition by wood boiling treatment or high temperature steam injection treatment, and improvement in the effect of preventing wood cracking upon drying or freezing, prevention of growth of microorganisms due to maintenance or improvement in anaerobic environment in wood.

Also, in accordance with the present invention, by allowing polyphenol oxidase and a dye or its precursor on which the polyphenol oxidase can act, to act on wood, it is possible to produce a coloring substance in the wood or to co-macromolecularize the coloring substance and polyphenol compounds such as lignin already contained in the wood so that firmer dying or coloring treatment of wood can be achieved. In the above-described wood dying or coloring treatment, many polyphenol oxidases are known to bleach lignin, which is a coloring substance contained in wood and, hence, the wood dying or coloring treatment according to the present invention is very useful since it allows enzymatic bleaching and dying or coloring treatment simultaneously, thus reducing the number of process steps and improving the color tone.

Further, in accordance with the present invention, by adding the enzyme having a polyphenol oxidizing activity together with phenolic compounds or aromatic amine compounds to concrete and macromolecularizing the phenolic compounds or aromatic amine compounds in the concrete, it is possible to improve slump loss and concrete strength and suppress rust formation of ferro-reinforcement due to a decrease in the concentration of oxygen in the concrete.

BEST MODE FOR CARRYING OUT THE INVENTION

Hereafter, the present invention will be described more concretely by representative examples which, however, are merely exemplary and the present invention should not be construed as being limited thereto.

In the following examples, the molecular weight analysis for macromolecularized phenolic compounds or aromatic amine compounds was carried out by HPLC using 50 mM of potassium phosphate buffer (pH 7.0) or 0.1 mM of sodium sulfate aqueous solution as an eluant, Shodex RI (differential refractive index detector, manufactured by Showa Denko as a detector, and Shodex PROTEIN KW-802.5 (tandem, manufactured by Showa Denko) or a combination of Shodex PROTEIN KW802.5 (manufactured by Showa Denko) with Shodex OHpak SB-804HQ (manufactured by Showa Denko) as a column.

EXAMPLE 1
Cultivation and Partial Purification, Concentration

In a 500 ml flask as a cultivation apparatus charged with 100 ml of a culture medium containing 0.134% $Na_2HPO_4.12H_2O$, 0.03% $KH_2PO_4$, 1% maltose, 1% peptone, 0.1% yeast extracts, 0.05% $MgSO_4 \cdot 7H_2O$, 0.1 mM $CuSO_4$, 1 mM $MnCl_2$, and 2 mM $CaCl_2$, adjusted to pH 7.8 by addition of 20% $Na_2CO_3$, was inoculated with *Bacillus licheniformis* SD3003 (Accession No. FERM BP-5801). After cultivation with shaking at 50° C. for 16 hours, the cultivation temperature was lowered to 35° C. and the cultivation was continued for 3 days. After the cultivation, the culture broth was centrifuged at 4° C. to obtain a culture broth eliminated the bacillus. To further purify and concentrate this, ammonium sulfate fractionation was effective and at 20 to 60% saturation ammonium sulfate concentration, most polyphenol oxidase activity was recovered as precipitation. The obtained ammonium sulfate precipitation was dialyzed against 10 mM Bis-tris/HCl buffer solution (pH 7.0). For further purification and concentration, there was used ultrafiltration membrane to obtain a partially purified concentrated aqueous solution (0.8 U/ml) in the fractions corresponding to molecular weights of 10,000 to 100,000.

EXAMPLE 2
Cultivation and Concentration

In a culture cistern containing a 3 liter culture medium consisting of 0.5% glucose, 0.1% $NaNO_3$, 1.34% $Na_2HPO_4.12H_2O$, 0.3% $KH_2PO_4$, 0.1% NaCl, 0.2% peptone, 20 ppm yeast extracts, 0.01% $MgSO_4 \cdot 7H_2O$, and 0.1 mM $CuSO_4$, adjusted to pH 8 by addition of 10% NaOH, was inoculated with *Myrothecium verrucaria* SD3001 (Accession No. FERM BP-5520) and cultivation with shaking was carried out at 28° C. for 3 days. After the cultivation, centrifugation at 4° C. was carried out to obtain 2.5 liters of culture broth eliminated the bacillus.

Then, a part of the culture broth was concentrated to a fraction having a molecular weight of not smaller than 10,000 by using Minitan ultrafiltration system (manufactured by Millipore Co.) with Minitan filter packet (CAT. No.: PTGCOMPO4 manufactured by Millipore Co.).

Furthermore, after further dialysis against 200 ppm $NH_4HCO_3$, this was lyophilized to obtain a crude product as a freeze-dried product. The freeze-dried product had a polyphenol oxidase activity of 15 U/mg.

An aqueous solution of the freeze-dried product showed an absorption maximum near 600 nm, which is specific to copper-containing proteins.

EXAMPLE 3
Cultivation and Concentration

In a culture cistern containing a 3 liter culture medium consisting of 0.5% glucose, 0.1% $NaNO_3$, 1.34% $Na_2HPO_4 \cdot 12H_2O$, 0.3% $KH_2PO_4$, 0.1% NaCl, 0.2% peptone, 20 ppm yeast extracts, 0.01% $MgSO_4.7H_2O$, and 0.1 mM $CuSO_4$, adjusted to pH 8 by addition of 10% NaOH, was inoculated with *Myrothecium roridum* SD3002 (Accession No. FERM BP-5523) and cultivation with shaking was carried out at 28° C. for 3 days. After the cultivation, centrifugation at 4° C. was carried out to obtain 2.5 liters of culture broth eliminated the bacillus.

Then, a part of the culture broth was concentrated to a fraction having a molecular weight of not smaller than 10,000 by using Minitan ultrafiltration system (manufactured by Millipore Co.) with Minitan filter packet (CAT. No.: PTGCOMPO4 manufactured by Millipore Co.).

Furthermore, after further dialysis against 200 ppm $NH_4HCO_3$, this was lyophilized to obtain a crude product as a freeze-dried product. The freeze-dried product had a polyphenol oxidase activity of 10 U/mg.

An aqueous solution of the freeze-dried product showed an absorption maximum near 600 nm, which is specific to copper-containing proteins.

EXAMPLE 4
Macromolecularization Reaction

Macromolecularization reactions [4-1] to [4-3] described below were carried out using the partially purified concentrated aqueous solution described in Example 1, and macromolecularization reaction [4–4] was performed using commercially available polyphenol oxidase (obtained from TaKaRa).

[4-1]:

1 ml of reaction mixture was prepared which contained 20% (W/V) sodium lignosulfonate (obtained from Aldrich Chemical Company, Inc.) and the partially purified concentrated aqueous solution as a polyphenol oxidase in an activity concentration of 300 U/liter, and was shaken at a reaction temperature of 70° C. and at 100 rpm in a glass test tube to allow reaction. The pH of the reaction mixture was adjusted to pH 7.5 with a minute amount of sulfuric acid. After the initiation of reaction, the color tone of the reaction mixture turned denser immediately and after 6 hours, there was observed significant progress of macromolecularization and after 20 hours, most of the reaction mixture was solidified.

[4-2]:

Also, in the case where the reaction was carried out with changing the activity concentration of polyphenol oxidase to 60 U/liter, the whole reaction mixture was highly viscous liquid after 20 hours from the initiation of reaction, and the molecular weight of the product increased according as the viscosity increased. After continuing additional a 20 hour reaction, there was observed partial solidification of the reaction mixture. Samples for molecular weight analysis were prepared by taking out a part of the reaction mixture and heating in a water bath at about 100° C. for 15 minutes to terminate the reaction.

[4-3]:

Also, when lignin (alkali) (obtained from *Nacalai tesque*) was used in a concentration of 20% (W/V) instead of lignosulfonic acid and the reaction was carried out at an activity concentration of polyphenol oxidase of 300 U/liter at pH 7.5, the whole reaction mixture became highly viscous liquid after 24 hours from the initiation of reaction.

[4–4]:

100 ml of reaction mixture was prepared, which contained 20% (W/V) sodium lignosulfonate and a commercially available polyphenol oxidase as a polyphenol oxidase in an activity concentration of 300 U/liter and was shaken at a reaction temperature of 25° C. and at 100 rpm in a 500 ml flask to allow reaction. Since the commercially available polyphenol oxidase used herein was shown to be acid enzyme having an optimal reaction pH of 6 to 7 as measured using syringaldazine, the pH of the reaction mixture in the macromolecularization reaction was adjusted to pH 6.5 with a minute amount of sulfuric acid. After the initiation of a reaction, the color tone of the reaction mixture turned denser immediately, but it took about 80 hours of reaction before most of the reaction mixture could be solidified.

EXAMPLE 5

Macromolecularization Reaction

Using the freeze-dried products described in Example 2, there were carried out macromolecularization reactions [5-1] to [5-3] below.

[5-1]:

100 ml of reaction mixture was prepared, which contained 20% (W/V) sodium lignosulfonate and the freeze-dried product as a polyphenol oxidase in a concentration of 20 ppm (300 U/liter) and was shaken at a reaction temperature of 25° C. and at 100 rpm in a 500 ml flask to allow reaction. The pH of the reaction mixture was adjusted to pH 9 with NaOH. After the initiation of reaction, the color tone of the reaction mixture turned denser immediately and after 3 hours, there was observed significant progress of macromolecularization, and after 10 hours, most of the reaction mixture was solidified. Also, in the case where the reaction was carried out by changing the amount of polyphenol oxidase added to 4 ppm, after 20 hours the whole reaction mixture became highly viscous liquid, and after continuing additional a 20 hour reaction, there was observed partial solidification of the reaction mixture. Samples for molecular weight analysis were prepared by taking out a part of the reaction mixture and heating in a water bath at 90° C. for 5 minutes to terminate the reaction.

[5-2]:

Also, in the case where lignin (alkali) was used in a concentration of 20% (W/V) instead of lignosulfonic acid, the reaction was carried out at an activity concentration of polyphenol oxidase of 300 U/liter at pH 9 and at a reaction temperature of 25° C. After the initiation of the reaction, the color tone of the reaction mixture turned denser immediately, the macromolecularization reaction proceeded, and after 24 hours, most of the reaction mixture was solidified.

[5-3]:

Using 20% (W/V) sodium lignosulfonate, the reaction was carried out at a reaction temperature of 25° C. in an activity concentration of polyphenol oxidase of 300 U/liter, with the pH of the reaction mixture adjusted to 7 with a small amount of sulfuric acid. After the initiation of the reaction, the color tone of the reaction mixture turned denser immediately. However, there was observed no solidification of the reaction mixture.

EXAMPLE 6

Macromolecularization Reaction

Using the freeze-dried products described in Example 3, there were carried out macromolecularization reactions [6-1] to [6-2] below.

[6-1]:

100 ml of reaction mixture was prepared, which contained 20% (W/V) sodium lignosulfonate and the freeze-dried product as a polyphenol oxidase in a concentration of 30 ppm (300 U/liter) and was shaken at a reaction temperature of 25° C. and at 100 rpm in a 500 ml flask to allow reaction. The pH of the reaction mixture was adjusted to pH 9 with NaOH. After the initiation of reaction, the color tone of the reaction mixture turned denser immediately and after 3 hours, there was observed significant progress of macromolecularization, and after 10 hours, most of the reaction mixture was solidified.

[6-2]:

Also, in the case where lignin (alkali) was used in a concentration of 20% (W/V) instead of lignosulfonic acid, the reaction was carried at an activity concentration of polyphenol oxidase of 300 U/liter at pH 9 and at a reaction temperature of 25° C. After the initiation of the reaction, the color tone of the reaction mixture turned denser immediately, and after 24 hours, most of the reaction mixture was solidified.

EXAMPLE 7

Macromolecularization Reaction 100 ml of reaction mixture was prepared, which contained 20% (W/V) sodium lignosulfonate and a commercially available bilirubin oxidase (freeze-dried product) (obtained from Sigma) as a polyphenol oxidase in a concentration of 300 U/liter and the reaction mixture was shaken at a reaction temperature of 25° C. and at 100 rpm in a 500 ml flask to allow reaction. Since the bilirubin oxidase used herein was shown to have an optimal reaction pH of 8 to 9 as measured using syringaldazine, the macromolecularization reaction was carried out at pH 8.5 which was the pH of the reaction mixture without adjustment. After the initiation of reaction, the color tone of the reaction mixture turned denser immediately and after 8 hours, there was observed significant progress of macromolecularization, and after 24 hours, most of the reaction mixture was solidified.

Also, when lignin (alkali) was added in a concentration of 20% (W/V) instead of lignosulfonic acid and the reaction was carried out at pH 8.5, most of the reaction mixture was solidified after 50 hours from the initiation of reaction.

EXAMPLE 8

Antifungal Properties

Solid (gel-like) lignosulfonic acid obtained by a reaction similar to the macromolecularization reaction described in [5-1] in Example 5 was sliced to small pieces (10 mm×10 mm×3 mm), which were placed in the center of an L agar plate. Then, spores of *Aspergillus orizae* AHU7134 were spread over the whole surface of a culture medium of a plate and cultivated at 28° C. for 4 days. As a result, there was observed inhibition of growth of the fungus in the range of the upper part of and about 2 mm from the periphery of each small piece of lignosulfonic acid, which indicated that it was useful as an antifungal agent.

EXAMPLE 9

Antifungal Properties

To a 20% (W/V) aqueous solution of sodium lignosulfonate was added 200 ppm of hinokitiol (obtained from Tokyo Kasei Kogyo Co., Ltd.) and the resulting mixture was heated at 90° C. to melt hinokitiol, followed by suspending hinokitiol using a vortex mixer and cooling the suspension to 25° C. To the thus-obtained raw material for macromolecularization reaction was added the freeze-dried product described in Example 2 as a polyphenol oxidase in an activity concentration of 300 U/liter, and the mixture was subjected to macromolecularization reaction at a reaction temperature of 25° C. and at pH 9 to obtain solidified (gel-like) lignosulfonic acid containing hinokitiol. The solid product was sliced to small pieces (10 mm×10 mm×3 mm), which were placed in the center of an L agar plate. Then, spores of *Aspergillus orizae* AHU7134 were spread over the whole surface of a culture medium of a plate and cultivated at 28° C. for 4 days. As a result, there was observed inhibition of growth of the fungus in the range of the upper part of and about 10 mm from the periphery of each piece of lignosulfonic acid, which indicated that it was useful as an antifungal agent and as an antifungal agent retainer.

Also, to a 20% (W/V) aqueous solution of sodium lignosulfonate was added (+)-catechin•$H_2O$ (obtained from Sigma) in a concentration of 5,000 ppm and the freeze-dried product described in Example 2 as a polyphenol oxidase in an activity concentration of 300 U/liter. Then, the mixture was subjected to macromolecularization reaction at a reaction temperature of 25° C. and at pH 9 to obtain solidified (gel-like) lignosulfonic acid containing catechin. The antifungal properties of the solid product was tested in the same manner as in the above-described example and as a result, there was observed inhibition of growth of the fungus in the range of the upper part of and about 8 mm from the periphery of each piece of lignosulfonic acid, which indicated that it was useful as an antifungal agent and as an antifungal agent retainer.

EXAMPLE 10
Improvement of Concrete

A reaction mixture was prepared, which contained 20% (W/V) sodium lignosulfonate, 1% (W/V) anthraquinone-2-sulfonic acid, and the partially purified concentrated aqueous solution described in Example 1 as a polyphenol oxidase in an activity concentration of 60 U/liter and the reaction mixture was allowed to react in the same manner as the macromolecularization reaction described in [4-2] in Example 4. The resulting water-soluble macromolecule in an amount of 1/40 volume (final concentration of 0.5% by weight as lignosulfonic acid) was admixed with sand at a sand ratio (S/A) of 36% by weight and 440 g/liter of cement. The product showed a slump of 5.5 cm and a water reduction of 16.8%. To note, when tests similar to those in the above example were conducted using samples without macromolecularization reaction, a slump of 5.7 cm and a water reduction of 12.5% were obtained, and there was observed improvement in the effect of water reduction by macromolecularization.

EXAMPLE 11
Improvement of Concrete

A reaction mixture was prepared, which contained 20% (W/V) sodium lignosulfonate, 1% (W/V) anthraquinone-2-sulfonic acid, and the freeze-dried product described in Example 2 as a polyphenol oxidase in a concentration of 4 ppm and the reaction mixture was allowed to react in the same manner as the macromolecularization reaction described in [5-1] in Example 5. The resulting water-soluble macromolecule in an amount of 1/40 volume (final concentration of 0.5% by weight as lignosulfonic acid) was admixed with sand at a sand ratio (S/A) of 36% by weight and 440 g/liter of cement. The product showed a slump of 5.6 cm and a water reduction of 16.9%. To note, when tests similar to those in the above example were conducted using samples without macromolecularization reaction, a slump of 5.4 cm and a water reduction of 12.8% were obtained, and there was observed improvement in the effect of water reduction by macromolecularization.

EXAMPLE 12
Improvement of Soil

A reaction mixture was prepared, which contained the partially purified concentrated aqueous solution described in Example 1 as a polyphenol oxidase in an activity concentration of 60 U/liter and the reaction mixture was allowed to react in the same manner as the macromolecularization reaction described in [4-2] in Example 4 to obtain a water-soluble macromolecularized lignosulfonic acid (20% (W/V)), which was diluted with water to obtain a two-fold diluted preparation. To note, an operation, such as heating, for terminating the macromolecularization reaction was not carried out. The aqueous solution of macromolecularized lignosulfonic acid or water each in an amount of 3.0 ml was sprayed on a surface of 40 g by weight farm soil contained in a 50 ml glass beaker. The soil was incubated at 28° C. and a decrease in weight due to drying was measured. After 60 hours, the samples with the spraying of the aqueous solution of macromolecularized lignosulfonic acid and water, respectively, showed a decrease in weight of about 6 g and about 12 g, and there was observed improvement in water retention due to the macromolecularized lignosulfonic acid. Also, the sample with the spraying of the aqueous solution of macromolecularized lignosulfonic acid showed an increase in the hardness of the soil surface, which indicated usefulness as a soil improving agent and as a blow-applied seed bearing surface soil stabilizer.

EXAMPLE 13
Improvement of Soil

A reaction mixture was prepared which contained the freeze-dried product described in Example 2 as a polyphenol oxidase in a concentration of 4 ppm and the reaction mixture was allowed to react in the same manner as the macromolecularization reaction described in [5-1] in Example 5 to obtain a water-soluble macromolecularized lignosulfonic acid (20% (W/V)), which was diluted with water to obtain a two-fold diluted preparation. To note, an operation, such as heating, for terminating the macromolecularization reaction was not carried out. The aqueous solution of macromolecularized lignosulfonic acid or water each in an amount of 3.0 ml was sprayed on a surface of 40 g by weight farm soil contained in a 50 ml glass beaker. The soil was incubated at 28° C. and a decrease in weight due to drying was measured. After 60 hours, the samples with the spraying of the aqueous solution of macromolecularized lignosulfonic acid and water, respectively, showed a decrease in weight of about 5 g and about 12 g, and there was observed an increase in water retention due to the macromolecularized lignosulfonic acid. Also, the sample with the spraying of the aqueous solution of macromolecularized lignosulfonic acid showed an increase in the hardness of the soil surface, which indicated usefulness as a soil improving agent and as a blow-applied seed bearing surface soil stabilizer.

EXAMPLE 14
Wood Treatment

A reaction mixture was prepared which contained the freeze-dried product described in Example 2 as a polyphenol oxidase in a concentration of 4 ppm and the reaction mixture was allowed to react in the same manner as the macromolecularization reaction described in [5-1] in Example 5 to obtain a water-soluble macromolecularized lignosulfonic acid (20% (W/V)). To note, an operation, such as heating, for terminating the macromolecularization reaction was not carried out. An aqueous solution of the macromolecularized lignosulfonic acid was diluted to 10 fold. Using the resulting solution as a wood treating agent, injection treatment with the agent was conducted on a cryptomeria log (unseasoned wood of 3 cm in diameter and 20 cm in length) which was treated in aqueous 0.1% Tween 80 solution at 60° C. for 16 hours after removal of its bark. The injection treatment was carried out by the Bethell process involving pressure reduction to 720 mmHg and pressurization to 10 $kg/cm^2$. The log samples subjected to injection treatment with non-macromolecularized lignosulfonic acid and macromolecularized lignosulfonic acid, respectively, (two in each case) were set on the soil about 20 cm from the circumference of the nest of termite and left to stand for 2 months. Then, observation was made of termite preventing effect by the treatment with the agent. As a result, slight eating by termite occurred in the log samples treated with the non-macromolecularized lignosulfonic acid whereas no eating by termite was observed in the log samples treated with the macromolecularized lignosulfonic acid, the latter samples maintaining (homogeneity smoothness, luster) of log surface.

EXAMPLE 15
Wood Treatment

To a preparation obtained by adjusting an aqueous 1% p-phenylenediamine dihydrochloride (manufactured by Kanto Kagaku Co., Ltd.) to pH 9 with a small amount of NaOH was added the freeze-dried product described in Example 2 as a polyphenol oxidase in a concentration of 0.2 ppm. The preparation was immediately coated on a oak plate. Coloring reaction proceeded quickly on the surface and inside (depth: up to about 3 mm) of the plate to give rise to a plate material firmly colored in dark brown.

EXAMPLE 16
Waste Water Treatment

As a model of waste water containing phenolic compounds or aromatic amine compounds was used a 10 mM aqueous p-phenylenediamine dichloride solution. 100 ml of reaction mixture was prepared by adding as a polyphenol oxidase the freeze-dried product described in Example 2 in a concentration of 2 ppm and the reaction mixture at pH 8 was shaken at a reaction temperature of 25° C. and at 60 rpm in a 500 ml flask to carry out macromolecularization reaction. After the initiation of reaction, coloring of the reaction mixture started immediately and after 1 hour, significant coloring and coagulation of the macromolecule were observed due to progress of the oxidization and the macromolecularization. The reaction mixture was passed through a simple column containing KC flock (manufactured by Nippon Seishi Co., Ltd.), which is powdery cellulose, as a filter material, in a volume of about 40 cm$^3$. Thus, most part of the macromolecule derived from p-phenylenediamine could be filtered off from the aqueous solution.

To note, when p-phenylenediamine was treated in the same manner as in the above-described example except that the partially purified concentrated aqueous solution described in Example 1 in an activity concentration of 30 U/liter as a polyphenol oxidase was used instead of 2 ppm of the freeze-dried product described in Example 2, most part of the macromolecule derived from p-phenylenediamine was filtered off from the aqueous solution similarly.

EXAMPLE 17
Deoxygenating Agent

As a phenolic compound was used 50 mM of L-ascorbic acid Na, on which the freeze-dried product described in Example 2 was allowed to act in a concentration of 4 ppm at pH 9.0 at a temperature of 25° C. and oxygen consumption rate was measured using a manometer. As a result, the concentration of dissolved oxygen after 1 hour from the initiation of reaction decreased to 0.05% of that at the initiation of reaction, which indicated that the phenolic compound had high deoxygenating property.

To note, when oxygen consumption rate was measured in the same manner as in the above-described example except that the partially purified concentrated aqueous solution described in Example 1 in an activity concentration of 30 U/liter was used instead of 4 ppm of the freeze-dried product described in Example 2, the concentration of dissolved oxygen after 1 hour from the initiation of reaction decreased to 0.2% of that at the initiation of reaction, which indicated that the aqueous solution had high deoxygenating property similarly.

INDUSTRIAL APPLICABLITY

According to the present invention, efficient macromolecularization reaction of phenolic compounds or aromatic amine compounds is achieved and thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives, biotic repellents, insecticides, poultices, ink bases and wood treating agents containing the macromolecule is provided efficiently.

Also, by utilizing the present invention, there is provided an efficient production method for producing thickeners, stabilizers, coagulants, emulsifiers, dispersants, water retainers, antioxidants, adhesives, concrete admixtures, dyes, coating materials, petroleum recovering agents, soil conditioners, blow-applied seed bearing surface soil stabilizers, deodorants, smell eliminators, agricultural chemical spreaders, feeding stuff binders, bactericides, antimicrobial agents, viral infection inhibitors, bioadhesion preventives, biotic repellents, insecticides, poultices, ink bases and wood treating agents.

Further, in accordance with the present invention, there are provided a method of waste water disposal, a method of deoxygenation, and methods of treating wood, concrete and soil, respectively, utilizing the macromolecularization reaction of phenolic compounds or aromatic amine compounds.

Also, *Bacillus licheniformis* SD3003 (Accession No. FERM BP-5801), *Myrothecium verrucaria* SD3001 (Accession No. FERM BP-5520), and *Myrothecium roridum* SD3002 (Accession No. FERM BP-5523) used in the present invention are very useful for the production of the macromolecules of the present invention.

What is claimed is:

1. A method of protecting and strengthening wood through polymerization of one or more phenolic compounds or one or more aromatic amine compounds with an enzyme having polyphenol oxidizing activity, said method comprising impregnating wood with a combination comprising an enzyme having polyphenol oxidizing activity and one or more phenolic compounds or one or more aromatic amine compounds, allowing polymerization of the one or more phenolic compounds or the one or more aromatic amine compounds in the wood by said enzyme at an alkaline pH, and recovering the protected and strengthened wood.

2. The method as claimed in claim 1 wherein the enzyme having polyphenol oxidizing activity is one or more of the enzymes selected from the group consisting of catechol oxidase, laccase, polyphenol oxidase, ascorbic acid oxidase and bilirubin oxidase.

3. The method as claimed in claim 1, wherein the enzyme having a polyphenol oxidizing activity is an enzyme obtained by cultivating a bacterium belonging to the genus Bacillus.

4. The method as claimed in claim 3, wherein the enzyme having a polyphenol oxidizing activity is an enzyme obtained by cultivating *Bacillus licheniformis* or *Bacillus natto*.

5. The method as claimed in claim 4, wherein the enzyme having a polyphenol oxidizing activity is an enzyme obtained by cultivating *Bacillus licheniformis* SD3003 (Accession no. FERM BP-5801).

6. The method as claimed in claim 1, wherein the enzyme having a polyphenol oxidizing activity is an enzyme obtained by cultivating a fungus belonging to the genus Myrothecium.

7. The method as claimed in claim 6, wherein the enzyme having polyphenol oxidizing activity is an enzyme obtained by cultivating *Myrothecium verrucaria* or *Myrothecium roridum*.

8. The method as claimed in claim 7, wherein the enzyme having polyphenol oxidizing activity is an enzyme obtained by cultivating *Myrothecium verrucaria SD* 3001 (Accession No. FERM BP-5520) or *Myrothecium roridum SD* 3002 (Accession No. FERM BP- 5523).

9. The method as claimed in claim 1, wherein the phenolic compound is lignin or lignosulfonic acid.

10. A method of protecting and strengthening wood through polymerization of one or more phenolic compounds or one or more aromatic amine compounds with an enzyme having polyphenol oxidizing activity, said method comprising impregnating wood with an enzyme having polyphenol oxidizing activity, allowing polymerization of one or more phenolic compounds or one or more aromatic amine compounds already present in the wood by said enzyme at an alkaline pH, and recovering the protected and strengthened wood.

11. A method of protecting and strengthening wood through polymerization of one or more phenolic compounds or one or more aromatic amine compounds with an enzyme having polyphenol oxidizing activity, said method comprising impregnating wood with a combination comprising an enzyme having polyphenol oxidizing activity, one or more phenolic compounds or one or more aromatic amine compounds, and one or more thermal curing agents selected from the group consisting of a quinone compound, an unsaturated fatty acid, an unsaturated alcohol, and an unsaturated alkyl compound, allowing polymerization of the one or more phenolic compounds or the one or more aromatic amine compounds in the wood by said enzyme at an alkaline pH, and recovering the protected and strengthened wood.

12. A method of protecting and strengthening wood through polymerization of one or more phenolic compounds or one or more aromatic amine compounds with an enzyme having polyphenol oxidizing activity, said method comprising impregnating wood with a combination comprising an enzyme having polyphenol oxidizing activity, one or more phenolic compounds or one or more aromatic amine compounds, and a physiologically active substrate selected from the group consisting of an antimicrobial compound, antiviral composition, an insecticidal compound and a biotic repellent metal ion, allowing polymerization of the one or more phenolic compounds or the one or more aromatic amine compounds in the wood by said enzyme, and recovering the protected and strengthened wood.

13. The method as claimed in claim 12, wherein the method comprises allowing polymerization in an alkaline pH reaction medium.

* * * * *